United States Patent
Imai (10) Patent No.: US 7,869,560 B2
(45) Date of Patent: Jan. 11, 2011

(54) X-RAY CT APPARATUS AND IMAGE PROCESSING APPARATUS

(75) Inventor: Yasuhiro Imai, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 93 days.

(21) Appl. No.: 12/268,334

(22) Filed: Nov. 10, 2008

(65) Prior Publication Data

US 2009/0122953 A1   May 14, 2009

(30) Foreign Application Priority Data

Nov. 12, 2007   (JP)   ............... 2007-292955

(51) Int. Cl.
*A61B 6/00* (2006.01)
(52) U.S. Cl. ........................................ 378/5; 378/98.12
(58) Field of Classification Search ............... 378/4, 378/5, 98.11, 98.12
See application file for complete search history.

(56) References Cited

U.S. PATENT DOCUMENTS

| | | | |
|---|---|---|---|
| 3,974,386 A * | 8/1976 | Mistretta et al. | 378/98.11 |
| 4,029,963 A | 6/1977 | Alvarez et al. | |
| 4,542,459 A * | 9/1985 | Riederer | 600/431 |
| 4,559,557 A | 12/1985 | Keyes et al. | |
| 4,611,341 A | 9/1986 | Brody | |
| 4,633,307 A * | 12/1986 | Honda | 378/98.5 |
| 4,686,695 A | 8/1987 | Macovski | |
| 4,736,398 A | 4/1988 | Graeff et al. | |
| 4,813,061 A * | 3/1989 | Kakegawa | 378/98.11 |
| 5,396,530 A | 3/1995 | Tsutsui et al. | |
| 5,459,769 A | 10/1995 | Brown | |
| 5,661,774 A | 8/1997 | Gordon et al. | |
| 6,278,760 B1 | 8/2001 | Ogawa et al. | |
| 6,332,015 B1 * | 12/2001 | Honda | 378/98.11 |
| 6,356,617 B1 | 3/2002 | Besch et al. | |
| 6,421,419 B1 * | 7/2002 | Sakaida | 378/98.11 |
| 6,501,819 B2 * | 12/2002 | Unger et al. | 378/5 |
| 6,898,263 B2 * | 5/2005 | Avinash et al. | 378/4 |
| 6,922,462 B2 * | 7/2005 | Acharya et al. | 378/98.11 |
| 7,197,172 B1 | 3/2007 | Naidu et al. | |
| 7,224,763 B2 | 5/2007 | Naidu et al. | |
| 7,308,077 B2 | 12/2007 | Bijjani et al. | |

(Continued)

FOREIGN PATENT DOCUMENTS

JP   2004-065975   3/2004

*Primary Examiner*—Edward J Glick
*Assistant Examiner*—Alexander H Taningco
(74) *Attorney, Agent, or Firm*—Armstrong Teasdale LLP (57) ABSTRACT

An X-ray CT apparatus includes an X-ray radiation unit which applies a first X-ray having a first energy spectrum and a second X-ray having a second energy spectrum different from the first energy spectrum to a subject, an X-ray data acquisition unit which acquires first X-ray projection data of the subject based on the first X-ray and second X-ray projection data of the subject based on the second X-ray, and an image reconstruction unit which determines information about a difference between the first X-ray and the second X-ray with respect to an image of the subject, segments the image into at least two pixel areas based on the difference information, and sets part of the segmented pixel areas to a dual energy image obtained by a weighted subtraction process based on X-ray projection data having a plurality of energy spectrums.

18 Claims, 5 Drawing Sheets

U.S. PATENT DOCUMENTS

| | | |
|---|---|---|
| 7,415,145 B2 | 8/2008 | Hsieh et al. |
| 7,415,147 B2 | 8/2008 | Ying et al. |
| 2002/0039401 A1* | 4/2002 | Salb .......................... 378/98.9 |
| 2002/0075997 A1* | 6/2002 | Unger et al. ................ 378/98.9 |
| 2003/0095630 A1* | 5/2003 | Avinash et al. ............. 378/98.9 |
| 2005/0163283 A1* | 7/2005 | Bruder et al. ............ 378/98.11 |

* cited by examiner

FIG. 5

X-RAY CT APPARATUS AND IMAGE PROCESSING APPARATUS

CROSS REFERENCE TO RELATED APPLICATIONS

This application claims the benefit of Japanese Patent Application No. 2007-292955 filed Nov. 12, 2007, which is hereby incorporated by reference in its entirety.

BACKGROUND OF THE INVENTION

The subject matter disclosed herein relates to a technique which obtains dual energy images at an X-ray CT apparatus and an image processing apparatus therefore.

It has been known that a tomographic image of a conventional X-ray CT apparatus is image-reconstructed using a CT value (Hounsfield number). There has also been known a technique which obtains an image (hereinafter called "dual energy image") based on each of CT values respectively obtained using an X ray of an energy spectrum generated by an X-ray tube using a high X-ray tube voltage and an X ray of an energy spectrum generated by the X-ray tube using a low X-ray tube voltage (refer to, for example, Japanese Unexamined Patent Publication No. 2004-65975). Described more specifically, it has been known that according to the present technique, since X-ray absorption coefficients of substances in a subject are different depending on the X-rays different in energy spectrum, a difference is taken so that the substances lying in the subject are emphasized.

BRIEF DESCRIPTION OF THE INVENTION

A drawback arises in that S/N is degraded because of a process for taking the difference between the dual energy images by the weighted subtraction process. Therefore, a method for reconstructing a dual energy image improved in S/N and high in contrast has been expected.

Therefore, an object of the present invention is to provide an X-ray CT apparatus capable of obtaining a dual energy image improved in S/N and high in contrast.

An X-ray CT apparatus according to a first aspect, comprises an X-ray radiation unit for applying a first X-ray having a first energy spectrum and a second X-ray having a second energy spectrum different from the first energy spectrum to a subject; an X-ray data acquisition unit for acquiring first X-ray projection data of the subject based on the first X-ray applied from the X-ray radiation unit and second X-ray projection data of the subject based on the second X-ray applied therefrom; and a device for image-reconstructing which determines difference information between the first X-ray and the second X-ray with respect to a image of the subject, based on the first X-ray projection data and the second X-ray projection data, segments the image into at least two pixel areas, based on the difference information, and sets only part of the segmented pixel areas to a dual energy image obtained by a weighted subtraction process based on X-ray projection data having a plurality of energy spectrums.

Here, the term "weighted subtraction process" means a process for multiplying targeted data by weighting coefficients (including 1) to selectively delete the data thereby to take a difference therebetween.

An X-ray CT apparatus according to a second aspect is provided wherein in the X-ray CT apparatus according to the first aspect, the device for image-reconstructing determines a ratio between pixel values of a first image image-reconstructed using the first X-ray projection data and a second image image-reconstructed using the second X-ray projection data, as the difference information between the first X-ray and the second X-ray with respect to the image of the subject.

An X-ray CT apparatus according to a third aspect is provided wherein in the X-ray CT apparatus according to the first or second aspect, it further including a device for setting a segment condition which sets a reference related to the difference information between the first X-ray and the second X-ray, for segmenting the image of the subject into the pixel areas.

An X-ray CT apparatus according to a fourth aspect is provided wherein in the X-ray CT apparatus according to the third aspect, the reference related to the difference information can be set every plurality of types of substances contained in the subject.

An X-ray CT apparatus according to a fifth aspect is provided wherein in the X-ray CT apparatus according to the second aspect, it further includes a device for setting a segment condition which sets a range of the ratio between the pixel values of the first image and the second image as a reference for segmenting the pixel area of the subject.

An X-ray CT apparatus according to a sixth aspect is provided wherein in the X-ray CT apparatus according to the first through fifth aspects, the device for image-reconstructing performs image reconstruction of a first image using the first X-ray projection data and image reconstruction of a second image using the second X-ray projection data respectively and sets the other part of the segmented pixel areas as one of the first image image-reconstructed using the first X-ray projection data, the second image image-reconstructed using the second X-ray projection data, and an average image of the first and second.

An X-ray CT apparatus according to a seventh aspect is provided wherein in the X-ray CT apparatus according to the first through sixth aspect, the device for image-reconstructing obtains the dual energy image by a weighted subtraction process of the first image image-reconstructed using the first X-ray projection data and the second image image-reconstructed using the second X-ray projection.

An X-ray CT apparatus according to an eighth aspect is provided wherein in the X-ray CT apparatus according to the first through sixth aspects, the device for image-reconstructing image-reconstructs the first X-ray projection data and the second X-ray projection data after their weighted subtraction process, to obtain a dual energy image.

An image processing apparatus according to a ninth aspect comprises a device for image-reconstructing which determines difference information between a first X-ray having a first energy spectrum and a second X-ray having a second energy spectrum different from the first energy spectrum with respect to an image of a subject, based on first X-ray projection data of the subject based on the first X-ray and second X-ray projection data of the subject based on the second X-ray both acquired by applying the first X-ray and the second X-ray to the subject, segments the image into at least two pixel areas and sets only part of the segmented pixel areas as a dual energy image obtained by a weighted subtraction process based on X-ray projection data having a plurality of energy.

An image processing apparatus according to a tenth aspect is provided wherein in the image processing apparatus according to the ninth aspect, the device for image-reconstructing determines a ratio between pixel values of a first image image-reconstructed using the first X-ray projection data and a second image image-reconstructed using the second X-ray projection data, as the information about the difference between the first X-ray and the second X-ray with respect to the image of the subject.

An image processing apparatus according to an eleventh aspect is provided wherein in the image processing apparatus according to the ninth aspect or the tenth aspect, it further includes a device for setting a segment condition which sets a reference related to the information about the difference between the first X-ray and the second X-ray, for segmenting the image of the subject into the pixel areas.

An image processing apparatus according to a twelfth aspect is provided wherein in the image processing apparatus according to the eleventh aspect, the reference related to the difference information can be set every plurality of types of substances contained in the subject.

An image processing apparatus according to a thirteenth aspect is provided wherein in the image processing apparatus according to the tenth aspect, it further including a device for setting segment condition which sets a range of the ratio between the pixel values of the first image and the second image as a reference for segmenting the pixel area of the subject.

An image processing apparatus according to a fourteenth aspect is provided wherein in the image processing apparatus according to the ninth through thirteenth aspects, the device for image-reconstructing performs image-reconstruction of a first image using the first X-ray projection data and image-reconstruction of a second image using the second X-ray projection data respectively and sets the other part of the segmented pixel areas as one of the first image image-reconstructed using the first X-ray projection data, the second image image-reconstructed using the second X-ray projection data, and an average image of the first and second images.

An image processing apparatus according to a fifteenth aspect is provided wherein in the image processing apparatus according to the ninth through fourteenth aspects, the device for image-reconstructing obtains the dual energy image by a weighted subtraction process of the first image image-reconstructed using the first X-ray projection data and the second image image-reconstructed using the second X-ray projection data.

An image processing apparatus according to a sixteenth aspect is provided wherein in the image processing apparatus according to the ninth through fourteenth aspects, the device for image-reconstructing image-reconstructs the first X-ray projection data and the second X-ray projection data after their weighted subtraction process, to obtain a dual energy image.

According to an X-ray CT apparatus and an image processing apparatus of the present invention, an image improved in S/N and high in contrast can be obtained upon dual energy imaging of the X-ray CT apparatus.

DETAILED DESCRIPTION OF THE INVENTION

Figure 1:
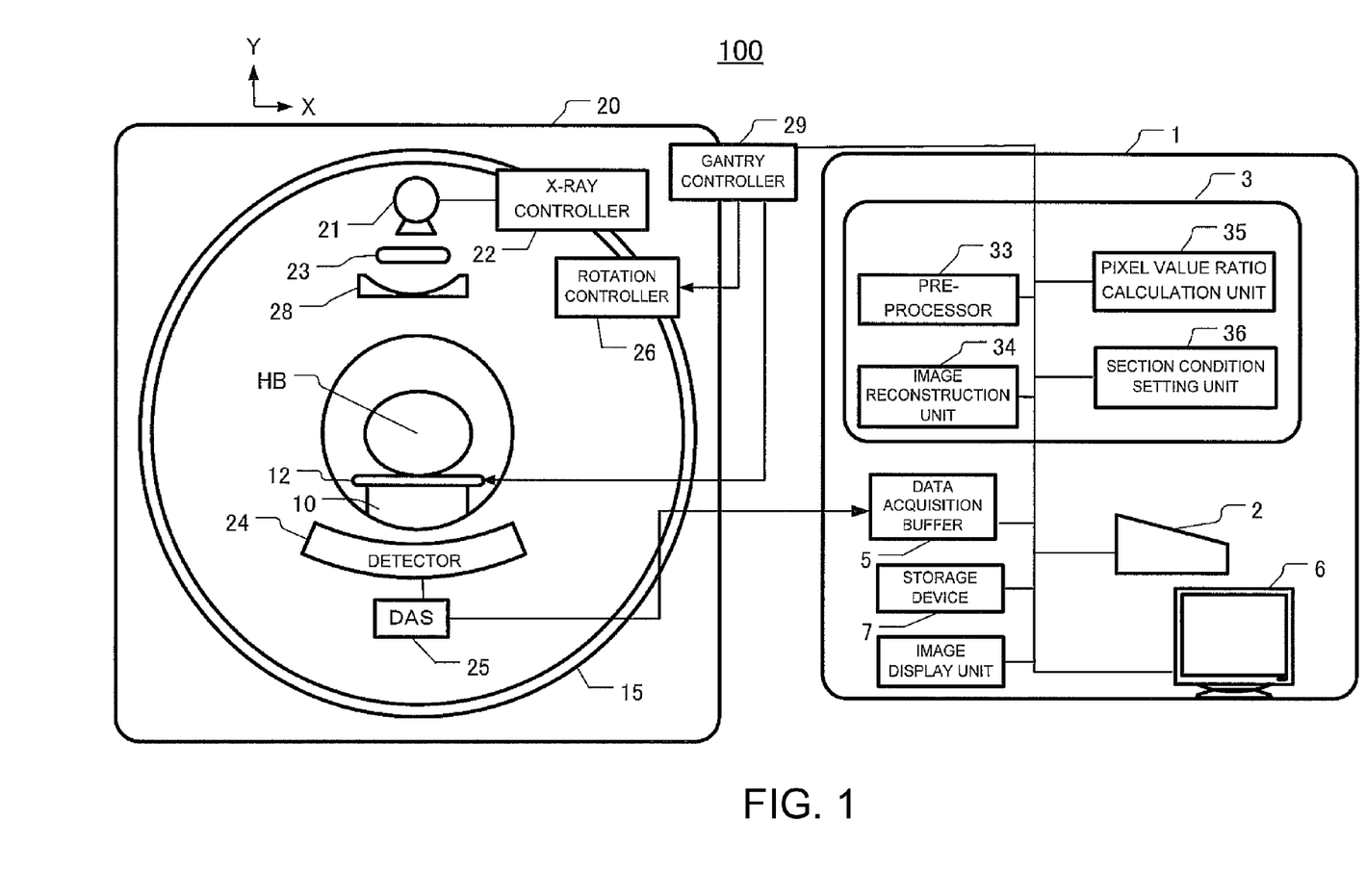
FIG. 1 is a block diagram showing an X-ray CT apparatus 100 according to an embodiment of the present invention.

FIG. 1 is a configuration block diagram showing an X-ray CT apparatus 100 according to one embodiment of the present invention. The X-ray CT apparatus 100 is equipped with an operation console 1, an imaging table 10 and a scan gantry 20.

The operation console 1 includes an input device 2 such as a keyboard or mouse or the like, which accepts an input from an operator, a central processing unit 3 which executes a pre-process, an image reconstructing process, a post-process, etc., and a data acquisition buffer 5 which acquires or collects X-ray detector data acquired by the scan gantry 20. Further, the operation console 1 includes a monitor 6 which displays a tomographic image image-reconstructed from projection data obtained by pre-processing the X-ray detector data, and a storage device 7 which stores programs, X-ray detector data, projection data and X-ray tomographic images therein. An input for imaging or photographing conditions is inputted from the input device 2 and stored in the storage device 7. The imaging table 10 includes a cradle 12 that draws and inserts a subject HB from and into an aperture of the scan gantry 20 with the subject placed thereon. The cradle 12 is elevated and moved linearly on the imaging table by a motor built in the imaging table 10.

The scan gantry 20 includes an X-ray tube 21, an X-ray controller 22, a collimator 23, a beam forming X-ray filter 28, an X-ray filter, a multi-row X-ray detector 24, and a data acquisition system (DAS). Further, the scan gantry 20 includes a rotation controller 26 which holds the X-ray tube 21 and the multi-row X-ray detector 24 and controls a gantry rotating segment 15 rotated about a body axis of the subject HB, and a gantry controller 29 which transmits/receives control signals or the like to/from the operation console 1 and the imaging table 10. The beam forming X-ray filter 28 is a filter which increases X rays directed to the center of rotation corresponding to the center of photography and decreases an X-ray dosage at its peripheral portion. Therefore, the body surface of the subject HB, which is nearly circular or elliptic, can be less exposed to radiation.

The central processing unit 3 has a pre-processor 33, an image reconstruction unit 34 and a pixel value ratio calculating unit 35.

The pre-processor 33 corrects channel-to-channel sensitivity ununiformity with respect to raw data acquired by the data acquisition system 25 and executes a pre-process such as an X-ray dosage correction for correcting an extreme reduction in signal strength or signal omission due to an X-ray strong absorber, principally, a metal portion. Further, the pre-processor 33 performs a beam hardening process.

The image reconstruction unit 34 receives projection data pre-processed at the pre-processor 33 and reconstructs an image, based on the projection data. The projection data is subjected to Fast Fourier Transform (FFT) for performing transformation into a frequency domain or region and overlaid with a reconstruction function Kernel(j), followed by being subjected to inverse Fourier transformation. The image reconstruction unit 34 performs a three-dimensional back-projection process on the projection data overlaid with the reconstruction function Kernel(j) to determine a tomographic image (xy plane) for each body-axis direction of the subject HB. The image reconstruction unit 34 stores the tomographic image in the storage device 7.

The image reconstruction unit 34 image-reconstructs a two-dimensional distribution tomographic image of X-ray tube voltage dependent information related to an atomic distribution, so-called tomographic image for dual energy photography or imaging from projection data or tomographic images based on X rays of low energy spectra and X rays of high energy spectra. The image reconstruction unit 34 is also capable of image-reconstructing an nth-dimensional tomographic image such as a three-dimensional tomographic image as well as the two-dimensional distribution tomographic image.

The pixel value ratio calculation unit 35 is capable of calculating each pixel value of a tomographic image at a low X-ray tube voltage by being divided by each pixel value of a tomographic image at a high X-ray tube voltage. The dual energy imaging is conducted in such a manner that the same portion or region is imaged with no positional displacement. Therefore, the same substance exists in the same pixel position. It is thus possible to calculate an energy ratio of the substance. Incidentally, the ratio between the pixel values is one example of information about the difference between a first X ray and a second X ray with respect to the tomographic images of the subject, based on first X-ray projection data and second X-ray projection data in the present invention.

A segment condition setting unit 36 sets a range of pixel values to sectionalize pixels each indicative of a substance in an image of the subject, based on the ratio between the pixel values calculated at the pixel value ratio calculation unit 35. Incidentally, the setting is done by making an input to the input device 2, based on information about the ratio between the pixel values displayed by the monitor 6, for example.

Figure 2:
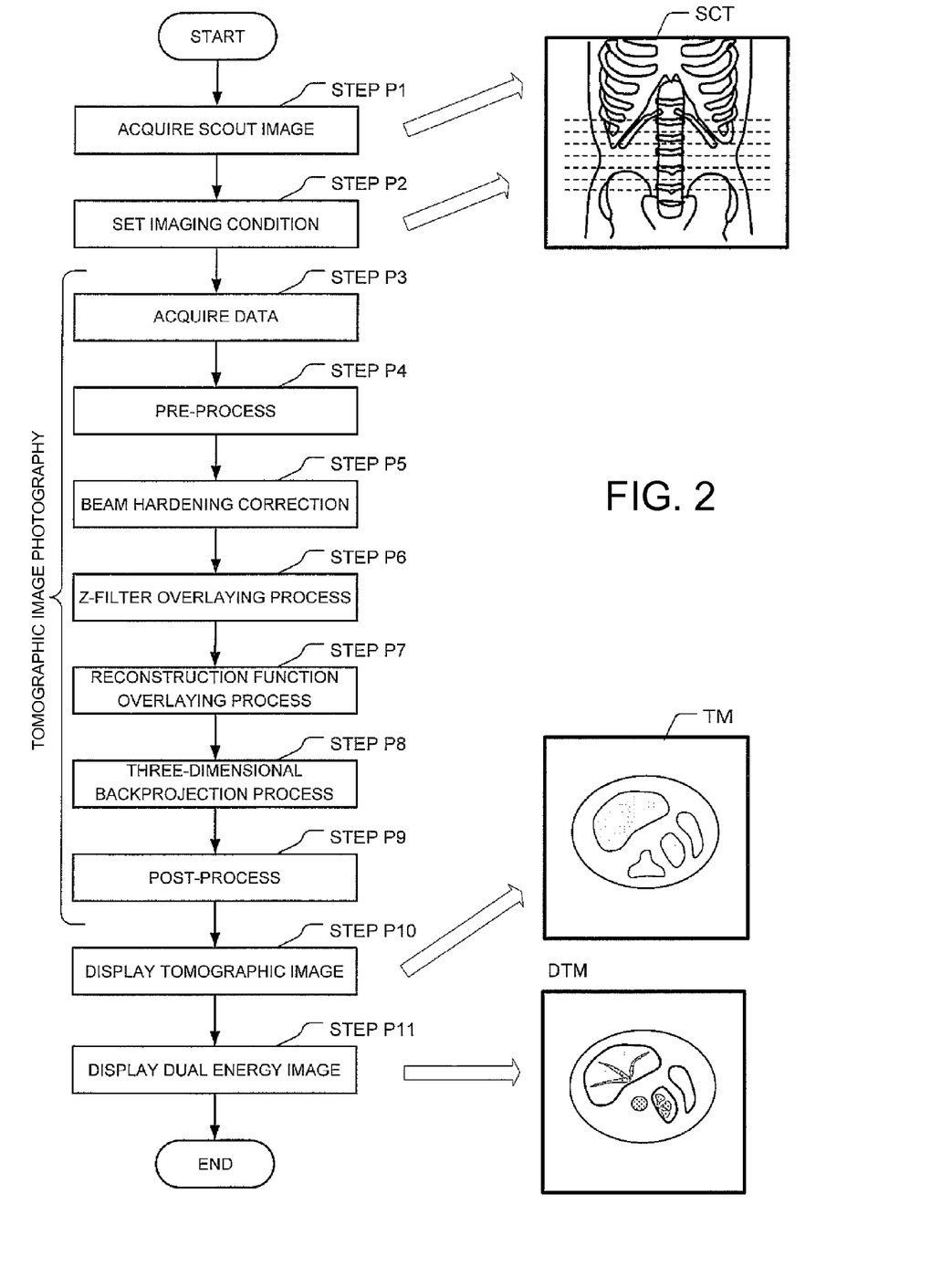
FIG. 2 is a flowchart illustrating an outline of operation of the X-ray CT apparatus 100 according to the present embodiment.

FIG. 2 is a flowchart showing an outline of operation of the X-ray CT apparatus 100 according to the present embodiment.

At Step P1, the subject HB is placed on the cradle 12 and they are aligned with each other. Here, in the subject HB placed on the cradle 12, a slice light central position of the scan gantry 20 is aligned with a reference point of its each portion or region. Then, scout image acquisition is performed. Upon scout image imaging, the X-ray tube 21 and the multi-row X-ray detector 24 are fixed and the operation of acquiring X-ray detector data is performed while the cradle 12 is being linearly moved. Here, the scout image is normally obtained at view angular positions of 0° and 90°. The right side in FIG. 2 shows an example of a scout image SCT formed by imaging or obtaining the neighborhood of a chest at 0°. The position to obtain a tomographic image from above the scout image can be planned.

At Step P2, an imaging condition setting is performed while the position and size of each tomographic image to be obtained on the scout image are displayed thereon. Dotted lines shown in the scout image correspond to positions of images corresponding to tomographic images. The present embodiment has a plurality of scan patterns based on a conventional scan, a helical scan, a variable pitch helical scan, a helical shuttle scan, etc. The conventional scan is a scan method of rotating the gantry rotating section 15 having the X-ray tube 21 and the multi-row X-ray detector 24 each time the cradle 12 is moved in a z-axis direction by predetermined intervals, thereby acquiring X-ray projection data. The helical scan is an imaging method of moving the cradle 12 at a predetermined velocity while the gantry rotating section 15 is being rotated, thereby acquiring X-ray projection data. The variable pitch helical scan is an imaging method of varying the velocity of the cradle 12 while the gantry rotating section 15 is being rotated in a manner similar to the helical scan, thereby acquiring X-ray projection data. The helical shuttle scan is a scan method of accelerating/decelerating the cradle 12 while the gantry rotating section 15 is being rotated in a manner similar to the helical scan and reciprocating the cradle 12 in a positive direction of a z axis or a negative direction thereof, thereby acquiring X-ray projection data. When these plural photographies are set, information about the whole X-ray dosage corresponding to one time is displayed.

Upon the imaging condition setting of each tomographic image, the exposure of the subject HB to X rays can also be optimized by using an automatic exposure mechanism of the X-ray CT apparatus 100. An X-ray tube voltage can be set to 80 kV and 140 kV for so-called dual energy imaging upon the imaging condition setting of the tomographic image. In the automatic exposure mechanism at the dual energy imaging, the imaging conditions at the X-ray tube voltage 80 kV and the X-ray tube voltage 140 kV can be defined in such a manner that a noise index value of a final image for a dual energy image based on weighted addition becomes approximately equal to a set noise index value. Defining the imaging conditions in such a manner that the image noises become approximately equal is preferred in terms of the optimization of X-ray exposure.

At Steps P3 through P9, tomographic image photography is performed. At Step P3, X-ray data acquisition is performed. When data acquisition is carried out by the helical scan here, the operation of acquiring X-ray detector data is performed while the X-ray tube 21 and the multi-row X-ray detector 24 are rotated about the subject HB and the cradle 12 on the imaging table 10 is linearly moved. Position information Ztable(view) of a z-axis coordinate is added to X-ray detector data D0(view, j, i) (where j=1 to ROW, and i=1 to CH) indicated by a view angle view, a detector row number j and a channel number i. Thus, X-ray detector data acquisition relative to a range at a constant velocity is performed upon the helical scan. The z-axis coordinate position information is used where the X-ray projection data is three-dimensionally image-reconstructed upon the helical scan and the variable pitch helical scan. At Step P3, X-ray projection data using the X-ray tube voltage of 80 kV at the same region and X-ray projection data using the X-ray tube voltage of 140 kV thereat are acquired.

At Step P4, the pre-processor 33 performs a pre-process on the X-ray detector data D0(view, j, i) to convert it into projection data. Described specifically, an offset correction is performed, logarithmic translation is performed, an X-ray dosage correction is performed, and a sensitivity correction is performed.

At Step P5, the pre-processor 33 performs a beam hardening correction. Here, the pre-processor 33 performs a beam hardening correction on the pre-processed projection data D1(view, j, i).

At Step P6, the image reconstruction unit 34 performs a z-filter overlaying process. Here, the image reconstruction unit 34 performs a z-filter overlaying process for applying filters in the z-axis direction (row direction) on the projection data D11(view, j, i) subjected to the beam hardening correction. That is, after the pre-process at each view angle, the projection data D11(view, j, i) (where i=1 to CH and j=1 to ROW) subjected to the beam hardening correction is multiplied by filters in which, for example, row-direction filter sizes are five rows.

At Step P7, the image reconstruction unit 34 performs a reconstruction function overlaying process. That is, X-ray projection data is subjected to Fourier transform for performing transformation into a frequency domain or region and multiplied by a reconstruction function, followed by being subjected to inverse Fourier transform.

At Step P8, the image reconstruction unit 34 performs a three-dimensional backprojection process. Here, the image reconstruction unit 34 performs a three-dimensional backprojection process on the projection data D3(view, j, i) subjected to the reconstruction function overlaying process to determine backprojection data D3(x, y, z). An image to be image-reconstructed is a plane orthogonal to the z axis. A reconstruction area or plane to be shown below is assumed to be parallel to the xy plane.

At Step P9, the image reconstruction unit 34 performs a post-process. The image reconstruction unit 34 performs post-processes such as image filter overlaying, CT value conversion and the like on the backprojection data D3(x, y, z) to obtain a tomographic image D31(x, y, z).

At Step P10, an image display unit displays an image-reconstructed tomographic image. As an example of the tomographic image, a tomographic image TM is shown on the right side of FIG. 2.

Incidentally, at the processes from Step P4 to Step P10, the X-ray projection data using the X-ray tube voltage of 80 kV and the X-ray projection data using the X-ray tube voltage of 140 kV both acquired at Step P3 are processed.

At Step P11, the image display unit displays a dual energy tomographic image DTM thereon. Here, the image reconstruction unit 34 first determines the ratio between pixels of a tomographic image obtained at the X-ray tube voltage 140 kV and a tomographic image obtained at the X-ray tube voltage 80 kV both of which are obtained at Step S10 and segments pixel areas according to the ratio. Part of the segmented areas is set as a dual energy image obtained as a result of performing a weighted subtraction process using weighted subtraction coefficients for eliminating a desired substance, on the tomographic image or projection data obtained at the X-ray tube voltage 140 kV and the tomographic image or projection data at the X-ray tube voltage 80 kV, whereas the other areas are set as images high in S/N ratio such as the image obtained at the X-ray tube voltage 140 kV and the image obtained at the X-ray tube voltage 80 kV, or an average image of these, etc., whereby a final dual energy image DTM is obtained.

The process at Step P11 referred to above will next be described in further detail using a first embodiment.

Figure 3:
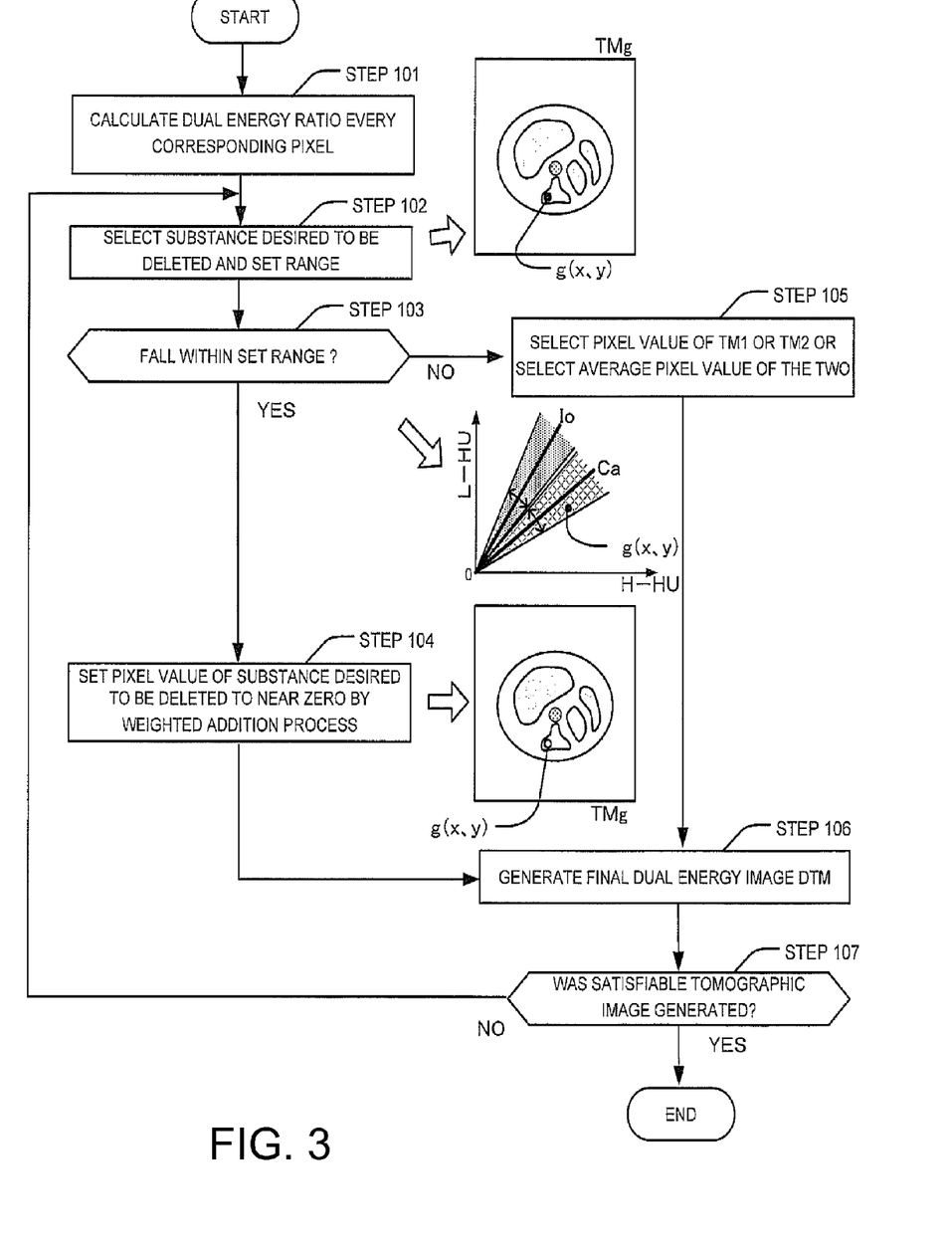
FIG. 3 is a flowchart for generating a dual energy tomographic image DTM.

The present embodiment will explain an example in which a dual energy image is reconstructed in a tomographic image space, using a flowchart shown in FIG. 3.

At Step 101, a process for determining the ratio between the values of pixels of a tomographic image obtained at an X-ray tube voltage 140 kV and a tomographic image obtained at an X-ray tube voltage 80 kV is performed. Incidentally, the ratio between the pixel values is one example of the difference information between a first X ray and a second X ray with respect to each tomographic images of a subject, based on first X-ray projection data and second X-ray projection data in the present invention.

Figure 4A:
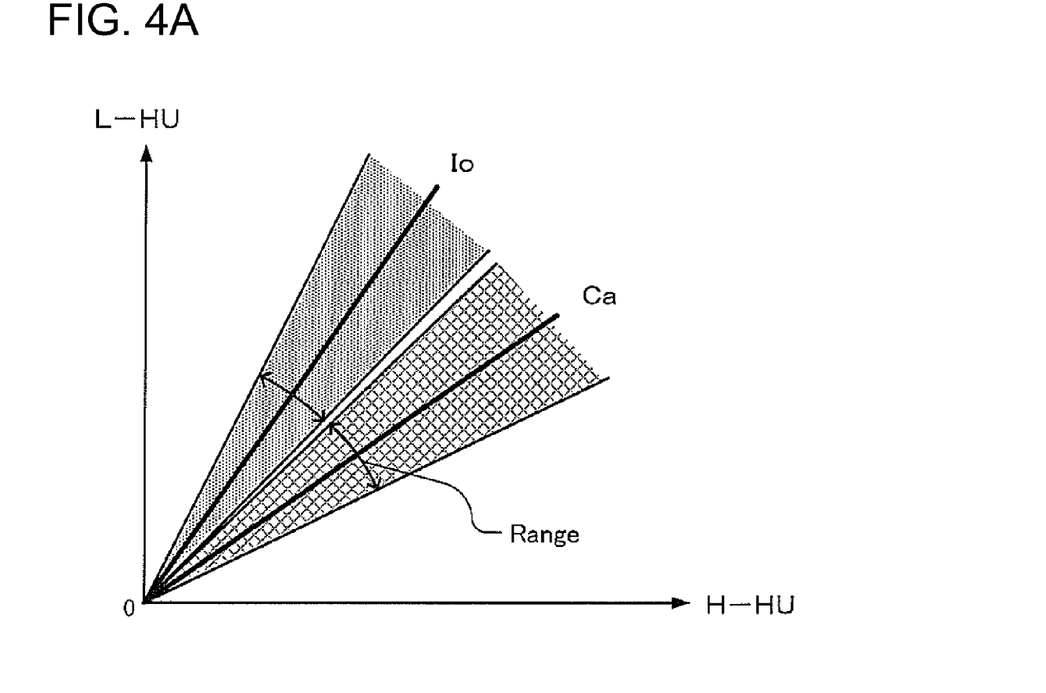
FIG. 4A is a graph showing the ratio between each of pixel values H-LU of a tomographic image at an X-ray tube voltage 140 kV and each of pixel values L-HU of a tomographic image at an X-ray tube voltage 80 kV.

FIG. 4(a) is a graph in which, for example, respective pixel values L-HU of a tomographic image at an X-ray tube voltage 80 kV are taken along the vertical axis of the graph, and respective pixel values H-HU of a tomographic image at an X-ray tube voltage 140 kV are taken along the horizontal axis thereof. As shown in the figure, the ratio (tilt in the graph) between each pixel value L-HU of each substance in the subject and each pixel value H-HU thereof as in the case of iodine (Io) and calcium (Ca) corresponding to principal components of a contrast agent, for example, becomes constant for each substance ideally. Actually, the ratio is considered to fall within the range indicated as "Range" (in the neighborhood of about 1.5 in the case of bones and about 1.7 to 1.8 in the case of contrast agent Io).

Described specifically, assuming that the pixel value of the tomographic image at the X-ray tube voltage 80 kV is g80 (x, y), and the pixel value of the tomographic image at the X-ray tube voltage 140 kV is g140 (x, y), the pixel value ratio calculation unit 35 can calculate the ratio r (x, y) between the pixel values in accordance with g80 (x, y)/g140 (x, y). Thus, the pixel value ratio calculation unit 35 calculates the ratio between the pixel values of all pixels for each pixel. However, the ratio between the pixel values can also be increased like areas of 1×2 pixels and 2×2 pixels. Since the increase in the area eliminates noise component and more enlarges the accuracy of removal of each substance desired to be deleted, it is further preferable that an operator is capable of selecting the number of pixels targeted for the calculation of the ratio between the pixel values.

Figure 4B:
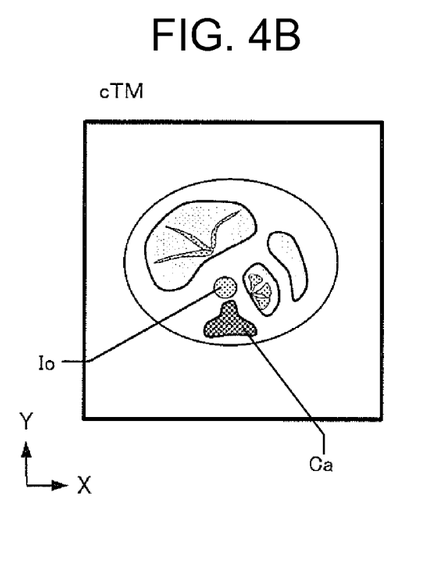
FIG. 4B is a conceptual diagram showing one example of a ratio image.

Next, at Step 102, the operator selects each substance desired to be deleted using the input device 2 and sets the range of the ratio between pixel values of the substance by a segment condition setting unit 36. The range is set so as to be variable at a predetermined value R±few %, for example. Incidentally, since the area can be partitioned off or segmented every substance by this segmentation, the segmented areas are assigned color maps respectively and thereby respective atoms or substances may be separated by color, and displayed. FIG. 4(b) is one example of a ratio image, cTM, in which iodine (Io) and calcium (Ca) are separated and displayed.

Figure 4C:
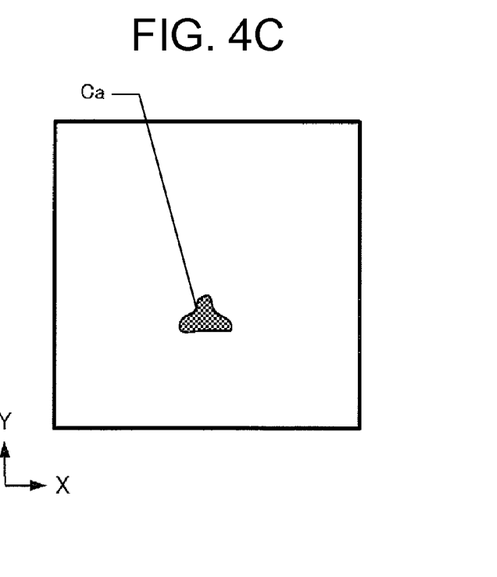
FIG. 4C is a conceptual diagram showing an image area of a calcium component.

FIG. 4(c) displays, as a pixel area, only a calcium (Ca) component at a pixel value-to-pixel value ratio represented in the neighborhood of about 1.5.

The range of a tilt of the ratio r (x, y) between pixel values used for sectionalization can be set by the segment condition setting unit 36. Incidentally, the present setting is done by making an input to the input device 2, based on information about the ratio between pixel values displayed by the monitor 6, for example. Here, the range of the ratio between the pixel values of substances desired to be finally deleted is set. Described specifically, the range of the ratio itself may be inputted or the ratio range may automatically be selected by choosing the substances. Alternatively, a default value corresponding to the range of the ratio is displayed by selection of each substance and the width of its range may be set so as to be adjustable.

Next, at Step 103, the image reconstruction unit 34 determines whether the value of its pixel value-to-pixel value ratio falls within a set value. If the value thereof is found to fall within the set value, then the image reconstruction unit 34 proceeds to Step 104. If not so, then the image reconstruction unit 34 proceeds to Step 105. In the present figure, for example, the ratio between pixel values at a pixel position g (x, y) falls within the range of the calcium (Ca). Incidentally, the pixel area containing pixels having fallen within the set range of pixel values can be specified by processing such as labeling.

Next, at Step 104, the image reconstruction unit 34 obtains a dual energy image with respect to the pixel area of each substance desired to be deleted, i.e., the pixel area containing the pixels that have fallen within the pixel-value range set at Step 102.

That is, the image reconstruction unit 34 multiplies a tomographic image TM1 of an X-ray tube voltage 80 kV by a weighted subtraction coefficient w1 in a tomographic image space. Similarly, the image reconstruction unit 34 multiplies a tomographic image TM2 of an X-ray tube voltage 140 kV by a weighted subtraction coefficient w2 and performs a weighted subtraction process ADD together with a constant C1 thereby to generate a dual energy tomographic image DTM. The image reconstruction unit 34 is capable of obtaining a dual energy tomographic image DTM by performing the weighted subtraction process ADD similarly even in a projection data space.

These weighted subtraction coefficients w1 and w2 and the constant C1 are determined according to an atom desired to be extracted, an atom desired to be emphasized, and an atom or region desired to be deleted on the display. When, for example, the calcium component (Ca component) that constitutes a bone and a calcified portion close to each other in CT value is deleted on the display, i.e., a pixel value is set to 0 in order to separate the calcium component and a contrast agent (Iodine component) with iodine as a principal component from each other in the weighted subtraction process, the contrast agent component is extracted and can be displayed emphatically. On the other hand, when the contrast agent component is deleted on the display, i.e., the pixel value is set to 0 in the weighted subtraction process, the calcium component is extracted and thereby the bone and calcified portion can be displayed emphatically. Incidentally, the weighted subtraction coefficient using the predetermined value R set at Step 102 may be used as a weighted addition coefficient. Alternatively, the weighted subtraction coefficient using the ratio between the respective pixels determined at Step 101 may be used.

Assume that the pre-process and the beam hardening correction have already been completed by the pre-processor 33 in the tomographic image space used at this time. Assume that even in the case of X-ray projection data, the pre-processor 33 uses the X-ray projection data subjected to the pre-process and the beam hardening correction. By setting a substance unequivalent to water to an X-ray penetration path length equivalent to water at each X-ray tube voltage, the dependence of each substance other than water on each X-ray tube voltage can be evaluated more correctly in the beam hardening correction in particular.

As described above, the image reconstruction unit 34 is capable of generating a contrast agent equivalent image (image from which the contrast agent is deleted), a calcium equivalent image (calcium-deleted image), etc. in the tomographic image space and the projection data space.

On the other hand, at Step 105, the image reconstruction unit 34 inputs the CT value of the tomographic image TM1 or tomographic image TM2 to the pixel position g (x, y) where the pixel value-to-pixel value ratio does not fall within the set value. Alternatively, each pixel inputted to the pixel position g (x, y) is brought to the tomographic image TM1, the tomographic image TM2 or the average value of the tomographic image TM1 and the tomographic image TM2.

Figure 5:
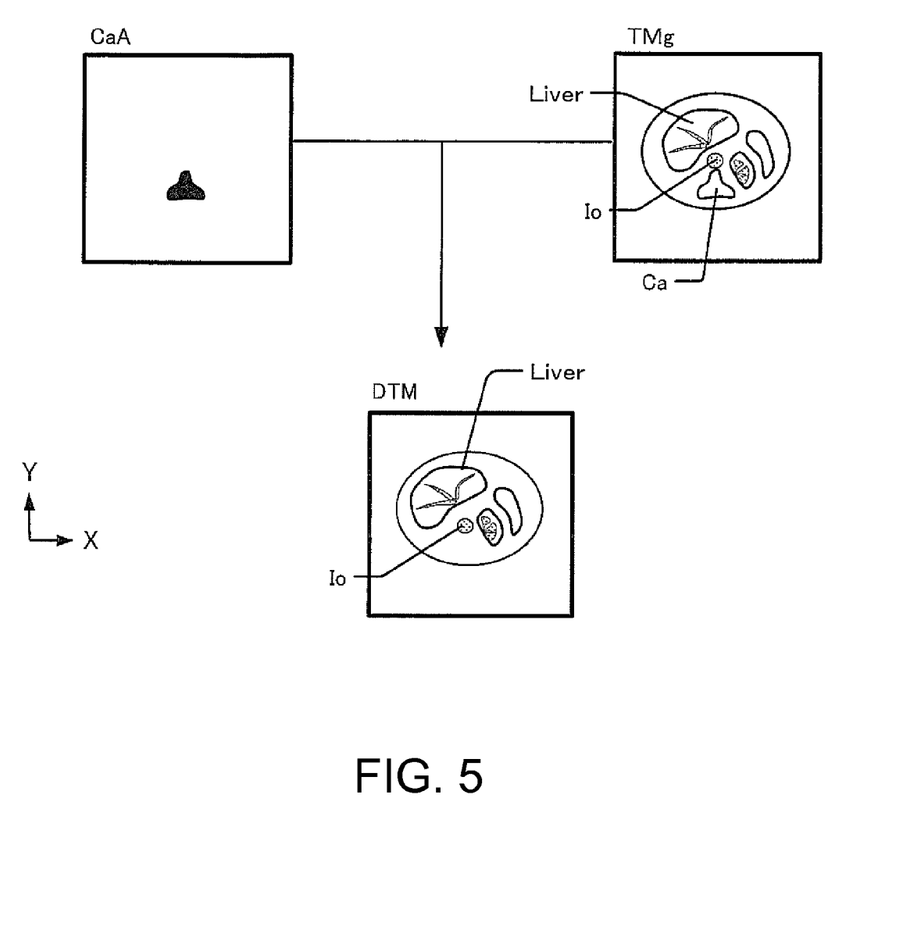
FIG. 5 is a conceptual diagram illustrating an image generating method of a dual energy tomographic image DTM.

At Step 106, the image reconstruction unit 34 can display the final dual energy tomographic image DTM by displaying all the pixel positions g (x, y) processed. That is, as shown in FIG. 5, a pixel area (indicated in black in the figure) of the deleted calcium component indicated by the dual energy image is substituted with the pixel area of the calcium component in the tomographic image TM1, the tomographic image TM2 or the average image of the tomographic image TM1 and the tomographic image TM2, and thereby the final dual energy tomographic image DTM can be obtained.

Since the tomographic image TM1, the tomographic image TM2 or the average value thereof is added to the pixel position g (x, y) at which the ratio between the pixel values does not fall within the set value, the pixel position can be brought to an image that is not reduced in S/N and is high in contrast.

At Step S107, the operator determines whether the dual energy tomographic image DTM can be satisfied. When it is not possible to obtain the targeted emphasized image, the operator returns to Step S102, where the operator changes the value of the pixel value-to-pixel value ratio or its allowable width (range) and is able to try to make separation of a targeted substance.

Thus, while the dual energy image DTM is image-reconstructed by selecting the substance desired to be deleted, a more accurately extracted dual energy tomographic image DTM can be generated by further adding a substance desired to be deleted.

A second embodiment will explain an example in which a dual energy image is reconstructed in a projection data space.

First, a process for determining the ratio between pixels of a tomographic image obtained at an X-ray tube voltage 140 kV and a tomographic image obtained at an X-ray tube voltage 80 kV, which is similar to the process at Step 101 of the first embodiment, is performed.

Next, each pixel to which the value of the ratio is assigned, is reprojected onto a virtual detector to obtain virtual projection data indicated by a sinogram, which is provided with the coordinate of each pixel and the value of the ratio as data.

Next, an allowable width (range) of the ratio between pixel values is set by the segment condition setting unit 36 in a manner similar to the process at Step 102 of the first embodiment.

Next, it is determined at Step 103 of the first embodiment whether the value of a pixel ratio between the respective virtual projection data falls within a set value.

Next, at Step 104, the image reconstruction unit 34 obtains a dual energy image using a pixel area of a substance desired to be deleted, i.e., projection data at the same pixel position as each virtual projection data having fallen within the range of the pixel values set at Step 102.

Described in detail, the image reconstruction unit 34 multiplies projection data at the X-ray tube voltage 80 kV by a weighted subtraction coefficient w1 in a projection data space, using the same weighted subtraction coefficient as the first embodiment. Similarly, the image reconstruction unit 34 multiplies projection data at the X-ray tube voltage 140 kV by a weighted subtraction coefficient w2 and performs a weighted subtraction process ADD together with a constant C1 thereby to generate a dual energy tomographic image DTM in accordance with an image reconstructing process using the projection data subsequent to the weighted subtraction.

Since processing subsequent to the above is similar to the above embodiment, its description will be omitted.

Incidentally, the present invention is not limited to the above-described embodiments.

Although the range of the ratio between the pixels of the substances desired to be deleted has been set at Step 102 in the above embodiment, a dual energy image may be obtained with respect to each pixel which delete each substance uncontained in the set range, i.e., which is not contained in the set range.

Although the processing of the two-dimensional image has been explained in the above embodiments, the present invention can be applied to the processing of a three-dimensional image.

Although the X-ray tube voltage 140 kV and the X-ray tube voltage 80 kV are used in the above embodiments, dual energy imaging can be conducted similarly even at other X-ray tube voltages. Although the calcification emphasized image and the bone emphasized image are used in the present embodiment, similar effects can be brought about even with respect to other substances. Incidentally, the image reconstructing method according to the present embodiment may be a three-dimensional image reconstructing method based on the conventional known Feldkamp method. Further, another three-dimensional image reconstructing method may be used. Alternatively, two-dimensional image reconstruction may be taken.

Although the above embodiment has described where the scan gantry 20 is not tilted, similar effects can be brought about even in the case of a so-called tilt scan at which the scan gantry 20 is tilted. Although the present embodiment has described where the X-ray data acquisition is not synchronized with the biological signal, similar effects can be brought about similarly even when it is synchronized with the biological signal, particularly, a heartbeat signal.

Although the multi-row X-ray detector 24 is used in the above embodiment, similar effects can be brought about even in the case of a two-dimensional X-ray area detector of a matrix structure typified by a flat panel X-ray detector, or a one-row X-ray detector. Incidentally, although the cradle 12 of the imaging table 10 is moved in the z direction in the present embodiment, similar effects can be obtained relatively even by moving the scan gantry 20 or the rotating section 15 lying in the scan gantry 20 relative to the cradle 12 of the imaging table 10.

Although the medical X-ray CT apparatus 100 has been described as the base in the above embodiment, the present invention is applicable even to an X-ray CT-PET apparatus, an X-ray CT-SPECT apparatus and the like combined with an industrial X-ray CT apparatus 100 or other apparatus.

What is claimed is:

1. An X-ray CT apparatus comprising:
   an X-ray radiation unit configured to apply a first X-ray having a first energy spectrum and a second X-ray having a second energy spectrum different from the first energy spectrum to a subject;
   an X-ray data acquisition unit configured to acquire first X-ray projection data of the subject based on the first X-ray applied by said X-ray radiation unit and second X-ray projection data of the subject based on the second X-ray applied by said X-ray radiation unit; and
   an image-reconstruction device configured to:
      determine difference information between the first X-ray and the second X-ray with respect to an image of the subject based on the first X-ray projection data and the second X-ray projection data.
      segment a major pixel area of the image into at least two minor pixel areas based on the difference information;
      set at least one of the at least two minor pixel areas to a dual energy image obtained by a weighted subtraction process based on the first X-ray projection data and the second X-ray projection data having different energy spectrums; and
      set all remaining minor pixel areas to one of a first image image-reconstructed using the first X-ray projection data, a second image image-reconstructed using the second X-ray projection data, and an average image of the first and second images.

2. The X-ray CT apparatus according to claim 1, wherein said image-reconstruction device is configured to determine a ratio between pixel values of the first image image-reconstructed using the first X-ray projection data and the second image image-reconstructed using the second X-ray projection data, as the difference information between the first X-ray and the second X-ray with respect to the image of the subject.

3. The X-ray CT apparatus according to claim 2, further comprising a segment condition setting device configured to set a range of the ratio between the pixel values of the first image and the second image as a reference for segmenting the major pixel area of the subject.

4. The X-ray CT apparatus according to claim 1, further comprising a segment condition setting device configured to set a reference for segmenting the image of the subject into the at least two minor pixel areas, the reference related to the difference information between the first X-ray and the second X-ray.

5. The X-ray CT apparatus according to claim 4, wherein the reference related to the difference information is set for each of a plurality of types of substances contained in the subject.

6. The X-ray CT apparatus according to claim 1, wherein said image-reconstruction device is configured to obtain the dual energy image using a weighted subtraction process of the first image image-reconstructed using the first X-ray projection data and the second image image-reconstructed using the second X-ray projection data.

7. The X-ray CT apparatus according to claim 1, wherein said image-reconstruction device is configured to image-reconstruct the first X-ray projection data and the second X-ray projection data after their weighted subtraction process, to obtain a dual energy image.

8. An image processing apparatus comprising:
   an image-reconstruction device configured to:
      determine difference information between a first X-ray having a first energy spectrum and a second X-ray having a second energy spectrum different from the first energy spectrum with respect to an image of a subject, the difference information based on first X-ray projection data of the subject that is based on the first X-ray and second X-ray projection data of the subject that is based on the second X-ray, both acquired by applying the first X-ray and the second X-ray to the subject;
      segment a major pixel area of the image into at least two minor pixel areas based on the difference information;
      set at least one of the at least two minor pixel areas to a dual energy image obtained using a weighted subtraction process based on X-ray projection data having a plurality of energy spectrums; and
      set all remaining minor pixel areas to one of a first image image-reconstructed using the first X-ray projection data, a second image image-reconstructed using the second X-ray projection data, and an average image of the first and second images.

9. The image processing apparatus according to claim 8, wherein said image-reconstruction device is configured to determine a ratio between pixel values of the first image image-reconstructed using the first X-ray projection data and the second image image-reconstructed using the second X-ray projection data, as the difference information between the first X-ray and the second X-ray with respect to the image of the subject.

10. The image processing apparatus according to claim 9, further comprising a segment condition setting device configured to set a range of the ratio between the pixel values of the first image and the second image as a reference for segmenting the major pixel area of the subject.

11. The image processing apparatus according to claim 8, further comprising a segment condition setting device configured to set a reference for segmenting the image of the subject into the at least two minor pixel areas, the reference related to the difference information between the first X-ray and the second X-ray.

12. The image processing apparatus according to claim 11, wherein the reference related to the difference information is set for each of a plurality of types of substances contained in the subject.

13. The image processing apparatus according to claim 8, wherein said image-reconstruction device is configured to obtain the dual energy image using a weighted subtraction process of the first image image-reconstructed using the first X-ray projection data and the second image image-reconstructed using the second X-ray projection data.

14. The image processing apparatus according to claim 8, wherein said image-reconstruction device is configured to image-reconstruct the first X-ray projection data and the second X-ray projection data after their weighted subtraction process, to obtain a dual energy image.

15. An image processing method for an X-ray CT apparatus, said method comprising:

determining, using a processor, difference information between a first X-ray having a first energy spectrum and a second X-ray having a second energy spectrum different from the first energy spectrum with respect to an image of a subject, the difference information based on first X-ray projection data of the subject that is based on the first X-ray and second X-ray projection data of the subject that is based on the second X-ray, both the first X-ray projection data and the second X-ray projection data acquired by applying the first X-ray and second X-ray to the subject;

segmenting a major pixel area of the image into at least two minor pixel areas based on the difference information;

setting at least one of the at least two minor pixel areas to a dual energy image obtained using a weighted subtraction process based on X-ray projection data having a plurality of energy spectrums; and setting all of the remaining minor pixel areas to one of a first image image-reconstructed using the first X-ray projection data, a second image image-reconstructed using the second X-ray projection data, and an average image of the first and second images.

16. The image processing method according to claim 15, further comprising determining a ratio between pixel values of the first image image-reconstructed using the first X-ray projection data and the second image image-reconstructed using the second X-ray projection data, as the difference information between the first X-ray and the second X-ray with respect to the image of the subject.

17. The image processing method according to claim 16, further comprising setting a range of the ratio between the pixel values of the first image and the second image as a reference for segmenting the major pixel area of the subject.

18. The image processing method according to claim 15, further comprising setting a reference for segmenting the image of the subject into the at least two minor pixel areas, the reference related to the difference information between the first X-ray and the second X-ray.

* * * * *